United States Patent [19]

Schmidt et al.

[11] 4,213,985
[45] Jul. 22, 1980

[54] NOVEL 5,11-DIHYDRO-6H-PYRIDO-[2,3-b][1,4]-BENZODIAZEPINE-6-ONES

[75] Inventors: Günther Schmidt; Màtyàs Leitold, both of Biberach an der Riss, Fed. Rep. of Germany

[73] Assignee: Boehringer Ingelheim GmbH, Ingelheim am Rhein, Fed. Rep. of Germany

[21] Appl. No.: 907,889

[22] Filed: May 19, 1978

[30] Foreign Application Priority Data

May 31, 1977 [DE] Fed. Rep. of Germany ....... 2724501

[51] Int. Cl.² ................... A61K 31/55; C02D 403/06
[52] U.S. Cl. ............................. 424/250; 260/239.3 T
[58] Field of Search .................. 260/239.3 T; 424/250

[56] References Cited

U.S. PATENT DOCUMENTS 3,660,380  5/1972  Schmidt et al. ............... 260/239.3 T
3,691,159  9/1972  Schmidt et al. ............... 260/239.3 T Primary Examiner—John M. Ford
Assistant Examiner—Robert T. Bond
Attorney, Agent, or Firm—Hammond & Littell, Weissenberger & Muserlian

[57] ABSTRACT

Novel 5,11-dihydro-6H-pyrido-[2,3-b][1,4]-benzodiazepine-6-ones of the formula

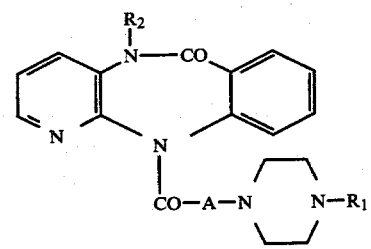

wherein $R_1$ is selected from the group consisting of hydrogen, alkyl of 1 to 6 carbon atoms, straight and branched chain, mono and poly unsaturated aliphatic hydrocarbon of 3 to 20 carbon atoms, phenyl alkyl of 1 to 4 alkyl carbon atoms and cinnamyl, $R_2$ is selected from the group consisting of hydrogen, methyl and ethyl and A is straight or branched chain alkylene of 2 to 5 carbon atoms and their non-toxic, pharmaceutically acceptable acid addition salts having ulcer inhibiting and secretion inhibiting activity and a novel process for their preparation.

9 Claims, No Drawings

NOVEL 5,11-DIHYDRO-6H-PYRIDO-[2,3-B][1,4]-BENZODIAZEPINE-6-ONES

OBJECTS OF THE INVENTION

It is an object of the invention to provide the novel 5,11-dihydro-6H-pyrido-[2,3-b][1,4]-benzodiazepine-6-ones of formula I and their non-toxic, pharmaceutically acceptable acid addition salts and a novel process for their preparation.

It is another object of the invention to provide novel ulcer inhibiting compositions and to a novel method of inhibiting ulcer formation or treating ulcers in warm-blooded animals.

These and other objects and advantages of the invention will become obvious from the following detailed description.

THE INVENTION

The novel products of the invention are 5,11-dihydro-6H-pyrido-[2,3-b][1,4]-benzodiazepine-6-ones of the formula

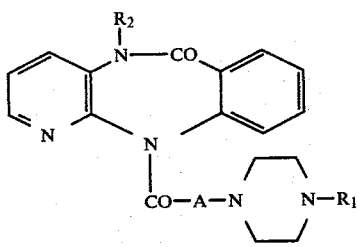

wherein $R_1$ is selected from the group consisting of hydrogen, alkyl of 1 to 6 carbon atoms, straight and branched chain, mono and poly unsaturated aliphatic hydrocarbon of 3 to 20 carbon atoms, phenyl alkyl of 1 to 4 alkyl carbon atoms and cinnamyl, $R_2$ is selected from the group consisting of hydrogen, methyl and ethyl and A is straight or branched chain alkylene of 2 to 5 carbon atoms and their non-toxic, pharmaceutically acceptable acid addition salts.

Examples of $R_1$ are hydrogen, alkyl such as methyl, ethyl, propyl, isopropyl, n-butyl, isobutyl, sec.-butyl, tert.-butyl, neopentyl, isopentyl, n-pentyl or n-hexyl group; unsaturated aliphatic groups such as allyl, 2-methylallyl, 3-methylbut-2-enyl (or prenyl), 1-methylallyl, pent-4-enyl, n-hex-5-enyl, n-hept-6-enyl, farnesyl, neryl, geranyl, citronellyl or phytyl; phenylalkyl such as benzyl, 2-phenylethyl, 1- or 2-or 3-phenylpropyl or phenylbutyl group.

Examples of suitable acids for the formation of non-toxic, pharmaceutically acceptable acid addition salts are inorganic acids such as hydrochloric acid, hydrobromic acid, sulfuric acid and phosphoric acid, and organic acids such as tartaric acid, fumaric acid, citric acid, maleic acid, succinic acid or oxalic acid.

The novel compounds of formula I may be prepared by reacting a 11-halogenoacyl-5,11-dihydro-6H-pyrido-[2,3-b][1,4]-benzodiazepine-6-one of the formula

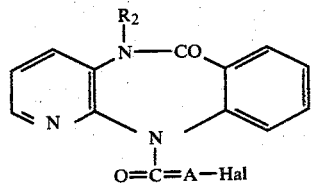

wherein $R_2$ and A are defined as above and Hal is a halogen atom with a piperazine of the formula

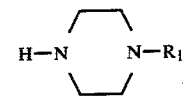

wherein $R_1$ has the above definition.

The said reaction is preferably carried out in an inert organic solvent optionally in the presence of an acid binding agent at elevated temperatures, preferably at the reflux temperature of the solvent used. Suitable solvents are alcohols such as ethanol, n-propanol, isopropanol, ketones such as acetone or ethers such as dioxane or tetrahydrofuran as well as aromatic hydrocarbons like benzene or toluene. It is preferred to use the piperazine of formula III in a sufficient excess to bind the liberated hydrogen halide; but, other hydrogen halide binding agents, for example alkali metal carbonates, alkali metal bicarbonates or tertiary organic amines such as triethylamine, pyridine or dimethylaniline may also be added.

The reaction may be effected by cleaving off hydrogen halide with a compound of formula II wherein instead of the group —A—Hal— there is a corresponding alkenylene group and then, the piperazine of formula III is adding to this alkenylene group. According to this variation of the process, the compounds of formula I may also be prepared by cleaving off hydrogen halide with hydrogen halide binding agents from compounds of formula II dissolved in an inert solvent by heating these substances, preferably to the boiling point of the reaction mixture, whereby the thus obtained compounds of formula II possess instead of the group —A—Hal an alkenylene group. The products are subsequently isolated and reacted with a piperazine of formula III in a solvent at temperatures up to the boiling point of the reaction mixture.

For the splitting off reaction of hydrogen halide, the solvents may be high-boiling ethers like dioxane or tetrahydrofuran as well as aromatic hydrocarbons like benzene or toluene. Suitable hydrogen halide removing agents are, for example, alkali metal carbonates, alkali metal bicarbonates or tertiary amines like triethylamine, pyridine or dimethylaniline. The reaction of the thus obtained intermediate with a piperazine of formula III is carried out in a solvent, for example, in an alcohol like ethanol, n-propanol, isopropanol or in a ketone like acetone or in an ether like dioxane or tetrahydrofuran or in an aromatic hydrocarbon like benzene or toluene.

The preparation of compounds of formula I wherein $R_1$ is hydrogen is possible if a compound of formula II is reacted in a large excess of piperazine. If a hydrogen halide binding agent is used in a solvent as above mentioned, the piperazine-excess should be at least 2 molar. The thus obtained yields are not always satisfactory and therefore, it is recommended for the preparation of such a compound to first of all prepare the corresponding 4-benzyl-piperazine-compound of formula I, wherein $R_1$ is benzyl and to subsequently split off the benzyl by known methods, for example by means of hydrogen in the presence of palladium on active charcoal.

Another method of preparing the compounds of formula I comprises reacting a 5,11-dihydro-11-[(1-piperazinyl)-acyl]-6H-pyrido-[2,3-b][1,4]-benzodiazepine-6-one of the formula

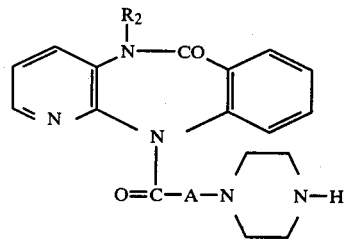
IV wherein $R_2$ and A are defined as above with a halide of the formula $R_1'$—Hal     V wherein $R_1'$ has the above definition for $R_1$ with the exception of a hydrogen atom and Hal represents a halogen atom.

The reaction is carried out in an inert organic solvent, preferably in an alcohol like ethanol, n-propanol or isopropanol, in an ether like dioxane or tetrahydrofuran or in a ketone like acetone, at elevated temperatures, preferably at the reflux temperature of the reaction mixture. It is recommended to bind the liberated hydrogen halide with hydrogen halide binding agents such as alkali metal carbonates, alkali metal bicarbonates or tertiary organic amines like triethylamine, pyridine or dimethylaniline.

The obtained compounds of formula I can be converted by reaction with inorganic or organic acids according to known methods into their non-toxic, pharmaceutically acceptable salts. The starting compounds of formula II may be prepared by reaction of a 5,11-dihydro-6H-pyrido-[2,3-b][1,4]-benzodiazepine-6-one of the formula.

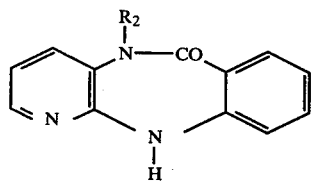
VI wherein $R_2$ is defined as above with a haloacyl halide of the formula $$\text{Hal}'-\overset{\overset{\text{O}}{\|}}{\text{C}}-\text{A}-\text{Hal} \quad \text{VII}$$

wherein A is defined as above and Hal and Hal', which can be the same or different, are halogens such as chlorine, bromine or iodine.

The reaction preferably is carried out in an inert solvent in the presence of a hydrogen halide binding agent at elevated temperatures, preferably at the reflux temperature of the reaction mixture. Suitable solvents are aromatic hydrocarbons, for example, benzene, toluene or xylene or ethers like diethyl ether, dipropyl ether or preferably, cyclic ethers like dioxane. Suitable hydrogen halide binding agents are tertiary organic amines such as triethylamine, N,N-dimethylaniline and pyridine as well as inorganic bases like alkali metal carbonates or alkali metal bicarbonates. The processing of the reaction mixture is carried out in the usual way with the yields in amounts up to 90% of theory.

The compounds of formula VI are described in German Pat. Nos. 1,179,943 and 1,204,680 or may be prepared by the process described therein. The preferred process for preparing the said compounds comprises reacting a compound of formula II with N-benzylpiperazine in a refluxing solvent such as ether, dioxane, ethanol, propanol or benzene and after the solvent is distilled off, a crystalline precipitate is produced consisting of a compound of the formula

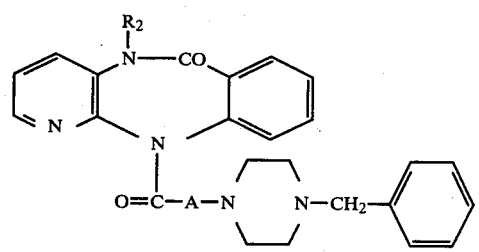
VIII wherein $R_2$ is defined as above. Then, the product is dissolved in an alcohol, for example methanol or ethanol and hydrogenated with palladium on charcoal at 20° to 80° C., preferably at 50° C. and a hydrogen pressure of 1 to 100 atm, preferably 50 atm. The corresponding compound of formula IV may be isolated from the reaction mixture.

The compounds of formula II may be prepared by reacting the appropriate 5,11-dihydro-6H-pyrido-[2,3-b][1,4]-benzodiazepine-6-one with a haloacyl halide and the compounds of formula II are formed as crystalline products which may be used as for the process. The intermediates having an alkenylacyl in the 11-position may be prepared by heating the 11-(haloacyl) compound in the presence of triethylamine. Also, the process described in German Pat. No. 1,936,670 may be used.

The novel ulcer inhibiting and secretion inhibiting compositions of the invention are comprised of an ulcer inhibiting and secretion inhibiting amount of at least one compound of formula I and their non-toxic, pharmaceutically acceptable acid addition salts and an inert pharmaceutical carrier or excipient. The composition may be in the form of tablets, dragees, gelules, granules, suppositories, injectable or potable solutions or suspensions prepared in the usual manner. Particularly preferred are 11-[3-(4-benzyl-1-piperazinyl)-propionyl]-5,11-dihydro-6H-pyrido-[2,3-b][1,4]-benzodiazepine-6-one and 5,11-dihydro-11-{3-[4-(2-phenylethyl)-1-piperazinyl]-propionyl}-6H-pyrido-[2,3-b][1,4]-benzodiazepine-6-one.

Examples of suitable excipients or carriers are talc, arabic gum, lactose, starch, magnesium stearate, cacao butter, aqueous or non-aqueous vehicles, fatty bodies of animal or vegetable origin, paraffinic derivatives, glycols, preservations and diverse wetting agents, dispersants and emulsifiers.

The compositions show valuable pharmacological properties and especially exert an ulcer inhibiting and secretion inhibiting effect. Thus, they are very valuable for the treatment of ulcer ventriculi et duodeni, against gastritis and other disturbances of the stomach and intestines.

The novel method of the invention for inhibiting secretion and ulcer formation in warm-blooded animals, including humans, comprises administering to warm-blooded animals an secretion inhibiting and ulcer inhibiting effective amount of at least one compound of formula I and its non-toxic, pharmaceutically acceptable acid addition salts. The compounds may be administered orally, rectally or parenterally. The usual useful dose is 0,03 to 0,25 mg/kg depending upon the method of administration and the specific compound.

In the following examples there are described several preferred embodiments to illustrate the invention. However, it should be understood that the invention is not intended to be limited to the specific embodiments.

EXAMPLE 1

5,11-dihydro-11-[3-(4-prenyl-1-piperazinyl)-propionyl]-6H-pyrido-[2,3-b][1,4]-benzodiazepine-6-one STEP A: 11-(3-chloropropionyl)-5,11-dihydro-6H-pyrido-[2,3-b][1,4]-benzodiazepine-6-one Equimolar amounts of 3-chloropropionyl chloride and 5,11-dihydro-6H-pyrido-[2,3-b][1,4]-benzodiazepine-6-one in solution in dioxane were reacted to obtain 11-(3-chloropropionyl)-5,11-dihydro-6H-pyrido-[2,3-b][1,4]-benzodiazepine-6-one which melted at 216°–218° C. with decomposition.

STEP B: 5,11-dihydro-11-[3-(4-prenyl-1-piperazinyl)-propionyl]-6H-pyrido-[2,3-b][1,4]-benzodiazepine-6-one A mixture of 6.6 g of 11-(3-chloropropionyl)-5,11-dihydro-6H-pyrido-[2,3-b][1,4]-benzodiazepine-6-one, 2.56 g of sodium carbonate and 4.0 g of 1-prenylpiperazine was refluxed in 90 ml of absolute ethanol for 2 hours. Then, the reaction mixture was vacuum filtered while still hot and the filtrate was evaporated to a volume of about 20 ml. The crystallized precipitate was vacuum filtered and the product was crystallized from isopropanol to obtain a 62% yield of 5,11-dihydro-11-[3-(4-prenyl-1-piperazinyl)-propionyl]-6H-pyrido-[2,3-b][1,4]-benzodiazepine-6-one melting at 199°–201° C.

EXAMPLE 2

11-[3-(4-benzyl-1-piperazinyl)-propionyl]-5,11-dihydro-6H-pyrido-[2,3-b][1,4]-benzodiazepine-6-one A mixture of 8.0 g of 11-(3-chloropropionyl)-5,11-dihydro-6H-pyrido-[2,3-b][1,4]-benzodiazepine-6-one and 30 ml of 1-benzyl-piperazine in 100 ml of isopropanol was refluxed for 1 hour. Then, the mixture was evaporated in vacuo to dryness and the residue was treated with sodium hydroxide solution. The base was extracted therefrom with chloroform and the chloroform extract was distilled to dryness. The residue was crystallized from xylene to obtain a 78% yield of 11-[3-(4-benzyl-1-piperazinyl)-propionyl]-5,11-dihydro-6H-pyrido-[2,3-b][1,4]-benzodiazepine-6-one with a melting point of 205°–207° C. The dihydro chloride salt of the acid base melted at 212°–214° C. after crystallization from methanol.

EXAMPLE 3

5,11-dihydro-11-[3-(1-piperazinyl)-propionyl]-6H-pyrido-[2,3-b][1,4]-benzodiazepine-6-one A warm solution of 6.0 g of 11-(3-chloropropionyl)-5,11-dihydro-6H-pyrido-[2,3-b][1,4]-benzodiazepine-6-one in 12 ml of dimethylacetamide and 40 ml of ethanol was added dropwise with stirring to a refluxing solution of 8.6 g of piperazine in 50 ml of ethanol. Then, the reaction mixture was refluxed for 1 hour and the mixture was evaporated to dryness in vacuo. The residue was chromatographed over silica gel and the eluent was then evaporated to dryness in vacuo. The residue was crystallized from acetonitrile to obtain a 70% yield of 5,11-dihydro-11-[3-(1-piperazinyl)-propionyl]-6H-pyrido-[2,3-b][1,4]-benzodiazepine-6-one with a melting point of 280°–282° C. with decomposition.

In another method to prepare the same compound, a mixture of 8.5 g of 11-[3-(4-benzyl-1-piperazinyl)-propionyl]-5,11-dihydro-6H-pyrido-[2,3-b][1,4]-benzodiazepine-6-one in 100 ml of absolute ethanol was hydrogenated at 60° C. and 50 atm with palladium charcoal as catalyst. After 5 hours, the calculated quantity of hydrogen was absorbed and after filtration of the catalyst, the alcohol was distilled off. The residue was crystallized from acetonitrile to obtain a 54% yield of the said product melting at 280°–282° C.

EXAMPLE 4

5,11-dihydro-11-[3-(4-prenyl-1-piperazinyl)-propionyl]-6H-pyrido-[2,3-b][1,4]-benzodiazepine-6-one A mixture of 3.5 g of 5,11-dihydro-11-[3-(1-piperazinyl)-propionyl]-6H-pyrido-[2,3-b][1,4]-benzodiazepine-6-one, 1.1 g of triethylamine and 2 g of prenyl bromide in 50 ml of n-propanol was refluxed for 3 hours and then the mixture was evaporated to dryness in vacuo. The product was triturated with water and the dissolved portion was crystallized by addition of isopropanol to obtain a 38% yield of 5,11-dihydro-11-[3-(4-prenyl-1-piperazinyl)-priopionyl]-6H-pyrido-[2,3-b][1,4]-benzodiazepine-6-one melting at 199°–201° C.

EXAMPLE 5

5,11-dihydro-11-{3-[4-(2-phenethyl)-1-piperazinyl]-propionyl}-6H-pyrido-[2,3-b][1,4]-benzodiazepine-6-one A mixture of 5.4 g of 11-(3-chloropropionyl)-5,11-dihydro-6H-pyrido-[2,3-b][1,4]-benzodiazepine-6-one and 3.8 g of 1-(2-phenethyl)-piperazine in 25 ml of dioxane was stirred for 2.5 hours at 80° C. and then, the red solution was evaporated in vacuo to dryness. The residue was dissolved in a mixture of chloroform and sodium bicarbonate and the chloroform phase was subsequently evaporated in vacuo to dryness. The residue was twice crystallized from n-propanol to obtain a 65% yield of 5,11-dihydro-11-{3-[4-(2-phenethyl)-1-piperazinyl]-propionyl}-6H-pyrido[2,3-b][1,4]-benzodiazepine-6-one melting at 192°–194° C.

EXAMPLE 6

5,11-dihydro-11-[3-(4-benzyl-1-piperazinyl)-propionyl]-6H-pyrido-[2,3-b][1,4]-benzodiazepine-6-one STEP A: 11-acryloyl-5,11-dihydro-6H-pyrido-[2,3-b][1,4]-benzodiazepine-6-one A solution of 11-(3-chloropropionyl)-5,11-dihydro-6H-pyrido-[2,3-b][1,4]-benzodiazepine-6-one in dioxane was refluxed for one hour in the presence of an excess of triethylamine to obtain a good yield of 11-(acryloyl)-5,11-dihydro-6H-pyrido-[2,3-b][1,4]-benzodiazepine-6-one which after crystallization from acetonitrile melted at 235° C. with decomposition.

STEP B: 5,11-dihydro-11-[3-(4-benzyl-1-piperazinyl)-propionyl]-6H-pyrido-[2,3-b][1,4]-benzodiazepine-6-one A mixture of 2.65 g of the product of Step A and 5.4 g of 1-benzyl-piperazine in 90 ml of absolute dioxane was refluxed for 2 hours and was then evaporated to dryness under reduced pressure. The residue was crystallized from isopropanol to obtain a 54% yield of 5,11-dihydro-11-[3-(4-benzyl-1-piperazinyl)-propionyl]-6H-pyrido-[2,3-b][1,4]-benzodiazepine-6-one melting at 205°-207° C.

EXAMPLE 7

5,11-dihydro-5-methyl-11-[2-(4-methyl-1-piperazinyl)-propionyl]-6H-pyrido-[2,3-b][1,4-benzodiazepine-6-one STEP A: 5-methyl-11-(2-chloropropionyl)-5,11-dihydro-6H-pyrido-[2,3-b][1,4]-benzodiazepine-6-one A solution of 2-chloropropionyl chloride and 5-methyl-5,11-dihydro-6H-pyrido-[2,3-b][1,4]-benzodiazepine-6-one in dioxane was reacted to obtain 11-(2-chloropropionyl)-5,11-dihydro-6H-pyrido-[2,3-b][1,4]-benzodiazepine-6-one which after crystallization from acetonitrile melted at 210°-212° C.

STEP B: 5,11-dihydro-5-methyl-11-[2-(4-methyl-1-piperazinyl)-propionyl]-6H-pyrido-[2,3-b][1,4]-benzodiazepine-6-one A mixture of 9.5 g of the product of Step A, 3.2 g of sodium carbonate and 4 ml of 1-methyl-piperazine in 120 ml of ethanol was refluxed for 7 hours and the hot solution was then vacuum filtered. The filtrate was evaporated to a volume of about 50 ml and the crystalline precipitate was separated. Then the filtrate was evaporated to dryness in vacuo and the residue was crystallized from isopropanol to obtain a 36% yield of 5,11-dihydro-5-methyl-11-[2-(4-methyl-1-piperazinyl)-propionyl]-6H-pyrido-[2,3-b][1,4]-benzodiazepine-6-one melting at 206°-208° C.

EXAMPLE 8

5,11-dihydro-11-[4-(4-methyl-1-piperazinyl)-butyryl]-6H-pyrido-[2,3-b][1,4]-benzodiazepine-6-one dihydrogen fumarate STEP A: 11-(4-chlorobutyryl)-5,11-dihydro-6H-pyrido-[2,3-b][1,4]-benzodiazepine-6-one A solution of 4-chlorobutyryl chloride and 5,11-dihydro-6H-pyrido-[2,3-b][1,4]-benzodiazepine-6-one in xylene was reacted to obtain 11-(4-chlorobutyryl)-5,11-dihydro-6H-pyrido-[2,3-b][1,4]-benzodiazepine-6-one which after crystallization from ethyl acetate melted at 205°-207° C.

STEP B: 5,11-dihydro-11-[4-(4-methyl-1-piperazinyl)-butyryl]-6H-pyrido-[2,3-b][1,4]-benzodiazepine-6-one dihydrogen fumarate A mixture of 6 g of 11-(4-chlorobutyryl)-5,11-dihydro-6H-pyrido-[2,3-b][1,4]-benzodiazepine-6-one and 6 g of 1-methylpiperazine in 200 ml of absolute dioxane was refluxed for 10 hours and then, the hot solution was vacuum filtered. The filtrate was evaporated to dryness in vacuo and the residue was washed with water and chromatographed over silica gel column. The obtained base was then heated with calculated quantity of fumaric acid in 60 ml of ethanol for 3 hours and on cooling, the dihydrogen fumarate separated. The precipitate was recrystallized from ethanol to obtain a 31% yield of the dihydrogen fumarate of 5,11-dihydro-11-[4-(4-methyl-1-piperazinyl)-butyryl]-6H-pyrido-[2,3-b][1,4]-benzodiazepine-6-one melting at 199°-201° C. with decomposition.

EXAMPLE 9

5,11-dihydro-11-[5-(4-methyl-1-piperazinyl)-valeryl]-6H-pyrido-[2,3-b][1,4]-benzodiazepine-6-one STEP A: 11-(5-chlorovaleryl)-5,11-dihydro-6H-pyrido-[2,3-b][1,4]-benzodiazepine-6-one A solution of 5-chlorovaleryl chloride and 5,11-dihydro-6H-pyrido-[2,3-b][1,4]-benzodiazepine-6-one in xylene was reacted to obtain 11-(5-chlorovaleryl)-5,11-dihydro-6H-pyrido-[2,3-b][1,4]-benzodiazepine-6-one which after crystallization from n-propanol melted at 170°-172° C.

STEP B: 5,11-dihydro-11-[5-(4-methyl-1-piperazinyl)-valeryl]-6H-pyrido-[2,3-b][1,4]-benzodiazepine-6-one A mixture of 5.0 g of 11-(5-chlorovaleryl)-5,11-dihydro-6H-pyrido-[2,3-b][1,4]-benzodiazepine-6-one, 1.6 g of sodium carbonate and 3 ml of 1-methylpiperazine in 100 ml of ethanol was refluxed for 20 hours and then the hot mixture was vacuum filtered. The filtrate was evaporated to dryness in vacuo and the residue was chromatographed over silica gel to obtain a 37% yield of 5,11-dihydro-11-[5-(4-methyl-1-piperazinyl)-valeryl]-6H-pyrido-[2,3-b][1,4]-benzodiazepine-6-one melting at 151°-153° C. after crystallization from ethyl acetate.

EXAMPLE 10

11-[3-(4-benzyl-1-piperazinyl)-propionyl]-5,11-dihydro-6H-pyrido-[2,3-b][1,4]-benzodiazepine-6-one A mixture of 3.51 g of 5,11-dihydro-11-[3-(1-piperazinyl)-propionyl]-6H-pyrido-[2,3-b][1,4]-benzodiazepine-6-one and 1.6 g of sodium carbonate were added to the mixture of 2.14 g of benzylbromide in 100 ml of absolute ethanol and the mixture was refluxed for 6 hours. Then, the hot mixture was vacuum filtered and the filtrate was evaporated to dryness in vacuo and purified by a silica gel column. The residue of the eluent was then crystallized from xylene to obtain a 42% yield of 11-[3-(4-benzyl-1-piperazinyl)-propionyl]-5,11-dihydro-6H-pyrido-[2,3-b][1,4]-benzodiazepine-6-one melting at 205°-207° C.

The column chromatographic purification of the raw products was in all examples effected with silica gel columns with an eluent of the following composition: chloroform: methanol: cyclohexane: concentrated ammonia = 68:15:15:2.

EXAMPLE 11

5,11-dihydro-11-[2-(4-methyl-1-piperazinyl)-propionyl]-6H-pyrido[2,3-b][1,4]-benzodiazepine-6-one STEP A: 11-(2-chloropropionyl)-5,11-dihydro-6H-pyrido-[2,3-b][1,4]-benzodiazepine-6-one A solution of 2-chloropropionyl chloride and 5,11-dihydro-6H-pyrido[2,3-b][1,4]-benzodiazepine-6-one in dioxane were reacted to obtain 11-(2-chloropropionyl)-5,11-dihydro-6H-pyrido-[2,3-b][1,4]-benzodiazepine-6-one which melted at 215°-218° C. under crystallization from ethanol.

STEP B: 5,11-dihydro-11-[2-(4-methyl-1-piperazinyl)-propionyl]-6H-pyrido-[2,3-b][1,4]-benzodiazepine-6-one Using the procedure of Example 5, the product of Step A was reacted with 1-methyl-piperazine to obtain a 49% yield of 5,11-dihydro-11-[2-(4-methyl-1-piperazinyl)-propionyl]-6-H-pyrido-[2,3-b][1,4]-benzodiazepine-6-one which melted at 223°–224° C. after crystallization from ethyl acetate.

EXAMPLE 12

5,11-dihydro-11-[3-(4-methyl-1-piperazinyl)-propionyl]-6H-pyrido-[2,3-b][1,4]-benzodiazepine-6-one dihydrochloride Using the procedure of Example 2, 11-(3-chloropropionyl)-5,11-dihydro-6H-pyrido-[2,3-b][1,4]-benzodiazepine-6-one and 1-methyl-piperazine were reacted to obtain a 51% yield of 5,11-dihydro-11-[3-(4-methyl-1-piperazinyl)-propionyl]-6H-pyrido-[2,3-b][1,4]-benzodiazepine-6-one which melted at 232°–233° C. after crystallization from an ethyl acetate-ethanol mixture. The dihydrochloride thereof melted at 235° C. after crystallization from ethanol.

EXAMPLE 13

11-[3-(4-allyl-1-piperazinyl)-propionyl]-5,11-dihydro-6H-pyrido-[2,3-b][1,4]-benzodiazepine-6-one Using the procedure of Example 7, 11-(3-chloropropionyl)-5,11-dihydro-6H-pyrido-[2,3-b][1,4]-benzodiazepine-6-one was reacted with 1-allyl-piperazine to obtain a 39% yield of 11-[3-(4-allyl-1-piperazinyl)-propionyl]-5,11-dihydro-6H-pyrido-[2,3-b][1,4]-benzodiazepine-6-one melting at 205°–207° C. after crystallization from ethanol.

EXAMPLE 14

5,11-dihydro-11-{3-[4-(2-methyl-allyl)-1-piperazinyl]-propionyl}-6H-pyrido-[2,3-b][1,4]-benzodiazepine-6-one Using the procedure of Example 2, 11-(3-chloropropionyl)-5,11-dihydro-6H-pyrido-[2,3-b][1,4]-benzodiazepine-6-one was reacted with 1-(2-methyl-allyl)-piperazine to obtain a 45% yield of 5,11-dihydro-11-{3-[4-(2-methyl-allyl)-1-piperazinyl]-propionyl}-6H-pyrido-[2,3-b][1,4]-benzodiazepine-6-one melting at 210°–211° C. after crystallization from ethanol.

EXAMPLE 15

5,11-dihydro-11-[3-(4-farnesyl-1-piperazinyl)-propionyl]-6H-pyrido-[2,3-b][1,4]-benzodiazepine-6-one dihydrochloride Using the procedure of Example 7, 11-(3-chloropropionyl)-5,11-dihydro-6H-pyrido-[2,3-b][1,4]-benzodiazepine-6-one was reacted with 1-farnesyl-piperazine to obtain a 48% yield of the dihydrochloride of 5,11-dihydro-11-[3-(4-farnesyl-1-piperazinyl)-propionyl]-6H-pyrido-[2,3-b][1,4]-benzodiazepine-6-one melting at 207°–209° C. after crystallization from absolute ethanol.

EXAMPLE 16

5,11-dihydro-11-[3-(4-phytyl-1-piperazinyl)-propionyl]-6H-pyrido-[2,3-b][1,4]-benzodiazepine-6-one dihydrochloride Using the procedure of Example 7, 11-(3-chloropropionyl)-5,11-dihydro-6H-pyrido-[2,3-b][1,4]-benzodiazepine-6-one was reacted with 1-phytyl-piperazine to obtain a 62% yield of 5,11-dihydro-11-[3-(4-phytyl-1-piperazinyl)-propionyl]-6H-pyrido-[2,3-b][1,4]-benzodiazepine-6-one dihydrochloride which melted at 204°–210° C. (with decomposition) after crystallization from ethanol.

EXAMPLE 17

5,11-dihydro-11-[6-(4-methyl-1-piperazinyl)-caproyl]-6H-pyrido-[2,3-b][1,4]-benzodiazepine-6-one STEP A: 11-(6-chloro caproyl)-5,11-dihydro-6H-pyrido-[2,3-b][1,4]-benzodiazepine-6-one A solution of 5,11-dihydro-6H-pyrido-[2,3-b][1,4]-benzodiazepine-6-one and 6-chloro-caproyl chloride in xylene was reacted to obtain 11-(6-chloro-caproyl)-5,11-dihydro-6H-pyrido-[2,3-b][1,4]-benzodiazepine-6-one melting at 128°–130° C.

STEP B: 5,11-dihydro-11-[6-(4-methyl-1-piperazinyl)-caproyl]-6H-pyrido-[2,3-b][1,4]-benzodiazepine-6-one Using the procedure of Example 9, the product of Step A was reacted with 1-methyl-piperazine to obtain a 36% yield of 5,11-dihydro-11-[6-(4-methyl-1-piperazinyl)-caproyl]-6H-pyrido-[2,3-b][1,4]-benzodiazepine-6-one melting at 179°–181° C. after crystallization from ethyl acetate.

EXAMPLE 18

60.0 mg of potato starch was heated in water to obtain a 10% slime which was then mixed with 148.0 mg of lactose, 10 mg of 11-[3-(4-benzyl-1-piperazinyl)-propionyl]-5,11-dihydro-6H-pyrido-[2,3-b][1,4]-benzodiazepine-6-one. The mixture was granulated through a sieve with a 1.5 mm mesh size and the granulate was dried at 45° C. and then put through the sieve again. 2.0 mg of magnesium stearate were added thereto and the mixture was pressed into tablets weighing 220 mg with a 9 mm punch.

The tablets could also be provided with an outer shell of sugar and talc and after polishing with bees wax weighed 300 mg.

EXAMPLE 19

2.0 mg of 11-[3-(4-benzyl-1-piperazinyl)-propionyl]-5,11-dihydro-6H-pyrido-[2,3-b][1,4]-benzodiazepine-6-one and 8.0 mg of sodium chloride were dissolved in distilled water and sufficient distilled water was added to obtain a volume of 1 ml. The solution was sterilized for 20 minutes at 120° C. and was sterile filtered into a 1 ml ampoule.

EXAMPLE 20

A suppository was prepared by suspending 15.0 mg of finely pulverized 11-[3-(4-benzyl-1-piperazinyl)-propionyl]-5,11-dihydro-6H-pyrido-[2,3-b][1,4]-benzodiazepine-6-one in 1685 mg of a molten suppository base (Witepsol W 45) which was then cooled to 40° C. and poured into slightly pre-cooled molds at 37° C. to obtain suppositories weighing 1.7 g.

EXAMPLE 21

1 g of 11-[3-(4-benzyl-1-piperazinyl)-propionyl]-5,11-dihydro-6H-pyrido-[2,3-b][1,4]-benzodiazepine-6-one dihydrochloride and 1.0 g of sodium cyclamate were dissolved in 70 ml of water and 15.0 g of glycerine were added thereto followed by addition of a solution of 0.035 g of methyl p-hydroxybenzoate, 0.015 g of propyl p-hydroxybenzoate, 0.05 g of anise oil and 0.06 g of menthol in 10.0 g of absolute ethanol. The volume was adjusted to 100.0 ml by addition of distilled water and the solution was filtered to obtain a drop solution containing 10 mg of active substance per drop.

PHARMACOLOGICAL DATA

A. Inhibiting effect on stress-ulcera

The tests were effected with 11-[3-(4-benzyl-1-piperazinyl)-propionyl]-5,11-dihydro-6H-pyrido-[2,3-b][1,4]-benzodiazepine-6-one (product A) and 11-{3-[4-(2-phenethyl)-1-piperazinyl]-propionyl}-5,11-dihydro-6H-pyrido-[2,3-b][1,4]-benzodiazepine-6-one (product B).

The inhibitory effect on the formation of stress-ulcera in rats was determined by the method of Takagi et al [Jap. Journ. Pharmac. Vol. 18, P. 9–18 (1968)] in which well-fed female rats with a body-weight between 220 and 260 g were each put into small wire-cages and subsequently kept vertically in a water bath held constant at a temperature of 23° C. for 16 hours so that only the heads and breast-bones of the animals were above the water surface. About 5 to 10 min. before this procedure, the test substances were orally administered to the animals using five animals for each dose. In the same manner, the control animals were administered 1 ml of a 0.9% physiological sodium chloride solution or 1 ml of a 1% solution of tylose. After 18 hours, the rats were killed by an overdosage of ethyl chloride and the stomachs were extracted, cut along the big curvature and extended on a cork disc. The evaluation was determined by the method of Marazzi-Uberti et al, and Takagi et al [Med. Exp. Vol. 4, pp. 284–292 (1961) and Jap. Journ. Pharmac. Vol. 18, P. 9–18 (1968)]. The results are reported in Table I.

B. Spasmolytic activity

The spasmolytic activity was determined in vitro in the guinea-pig colon using the experimental procedure of Magnus [Pflugers Archiv. Vol. 102 pp. 123 (1904)]. Acetylcholine was administered to cause spasms and control substance was atropine sulfate. The spastic was administered one minute before the application of the spasmolytic and the effective period of the spasmolytic wa 1 minute. Also in rats it was observed that the atropinic like side-effects such as retardation of the salvia-secretion are completely suppressed or remarkably decreased by the substances A and B. The results are reported in Table I.

C. Acute toxicity

The acute toxicity was determined by orally administering the test compounds to groups of 6 starving white mice with a weight of 18 to 20 g and the number of mice dead was determined after 14 days. The results are reported in Table I.

TABLE I

| Product | % Ulcer-inhibition in mg/kg | | | Spasmolysis of acetyl choline with Atropine | $DL_{50}$ in mg/kg |
| --- | --- | --- | --- | --- | --- |
| | 50 | 25 | 12.5 | = 1 | |
| A | 90 | 68 | 58 | 1/43 | >3000* |
| B | 87 | 56 | 34 | 1/70 | ~1500** |

*at 3000 mg/kg 1 animal out of 5 died;
**at 1500 mg/kg 3 animals out of 6 died;

The results of Table I show that spasmolytic effect of products A and B in comparison to that of atropine sulfate is remarkably lower and therefore also the atropine-like side-effects. Products A and B are substantially non-toxic.

Various modifications of the products and processes of the invention may be made without departing from the spirit or scope thereof and it is to be understood that the invention is intended to be limited only as defined in the appended claims.

We claim:

1. A compound of the formula

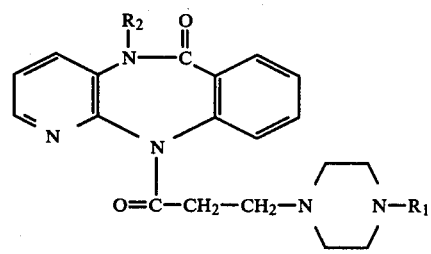

wherein $R_1$ is phenyl-(alkyl of 1 to 3 carbon atoms), and $R_2$ is hydrogen or methyl, or a non-toxic, pharmaceutically acceptable acid addition salt thereof.

2. A compound of claim 1, wherein $R_1$ is benzyl.

3. A compound of claim 1 wherein $R_2$ is hydrogen.

4. A compound of claim 1 selected from the group consisting of 11-[3-(4-benzyl-1-piperazinyl)-propionyl]5,11-dihydro-6H-pyrido-[2,3-b][1,4]-benzodiazepine-6-one and its non-toxic, pharmaceutically acceptable acid addition salts.

5. A compound of claim 1 selected from the group consisting of 5,11-dihydro-11-{3-[4-(2-phenethyl)-1-piperazinyl]-propionyl}-6H-pyrido-[2,3-b][1,4]-benzodiazepine-6-one and its non-toxic, pharmaceutically acceptable acid addition salts.

6. An ulcer inhibiting and secretion inhibiting composition comprising an ulcer inhibiting and secretion inhibiting effective amount of at least one compound of claim 1.

7. A method of inhibiting ulcer formation and inhibiting secretion in warm-blooded animals comprising administering to warm-blooded animals an ulcer inhibiting and secretion inhibiting effective amount of at least one compound of claim 1.

8. A method of claim 7, where said compound is selected from the group consisting of 11-[3-(4-benzyl-1-piperazinyl)-propionyl]-5,11-dihydro-6H-pyrido-[2,3-b][1,4]-benzodiazepine-6-one and its non-toxic, pharmaceutically acceptable acid addition salts.

9. A method of claim 7, where said compound is selected from the group consisting of 5,11-dihydro-11-{3-[4-(2-phenethyl)-1-piperazinyl]-propionyl}-6H-pyrido-[2,3-b][1,4]-benzodiazepine-6-one and its non-toxic pharmaceutically acceptable acid addition salts.

* * * * *

UNITED STATES PATENT AND TRADEMARK OFFICE
CERTIFICATE OF CORRECTION

PATENT NO. : 4,213,985
DATED : July 22, 1980
INVENTOR(S) : GÜNTHER SCHMIDT and MATYAS LEITOLD It is certified that error appears in the above-identified patent and that said Letters Patent are hereby corrected as shown below:

Column 5, line 67: "acid base" should read -- said base --.

Column 7, line 18: "[1,4-benzodiazepine-" should read

-- [1,4]-benzodiazepine- --.

Column 11, line 48: "wa 1 minute" should read

-- was 1 minute --.

*Signed and Sealed this*

*Twenty-eighth* Day of *October 1980*

[SEAL]

*Attest:*

SIDNEY A. DIAMOND

*Attesting Officer*  *Commissioner of Patents and Trademarks*